US009897367B2

United States Patent
Kobayashi (10) Patent No.: US 9,897,367 B2
(45) Date of Patent: Feb. 20, 2018

(54) FREEZING DETECTION DEVICE (71) Applicant: TEX E.G. CO., LTD., Tokyo (JP)

(72) Inventor: Takahide Kobayashi, Tokyo (JP)

(73) Assignee: TEX E.G. CO., LTD., Tokyo (JP)

( * ) Notice: Subject to any disclaimer, the term of this patent is extended or adjusted under 35 U.S.C. 154(b) by 766 days.

(21) Appl. No.: 14/333,389

(22) Filed: Jul. 16, 2014

(65) Prior Publication Data

US 2014/0326009 A1    Nov. 6, 2014

Related U.S. Application Data (63) Continuation of application No. PCT/JP2013/050276, filed on Jan. 10, 2013.

(30) Foreign Application Priority Data

Jan. 17, 2012  (JP) .................................. 2012-007506

(51) Int. Cl.
*F25D 3/00* (2006.01)
*F25C 1/00* (2006.01)
(Continued)

(52) U.S. Cl.
CPC ........... *F25D 21/02* (2013.01); *B67D 1/0857* (2013.01); *F25D 31/003* (2013.01); *G01K 7/16* (2013.01);
(Continued)

(58) Field of Classification Search
CPC .. B67D 1/0857; B67D 1/0859; B67D 1/0878; F25D 2700/12; F25D 31/003
(Continued)

(56) References Cited

U.S. PATENT DOCUMENTS 2,494,512 A * 1/1950 Kafer .................. A01J 9/04
62/376
3,882,693 A * 5/1975 Hiller .................. F25D 31/003
165/70

(Continued)

FOREIGN PATENT DOCUMENTS

EP  1 985 589 A1  10/2008
JP  55-59302 A  5/1980
(Continued)

OTHER PUBLICATIONS

European Search Report dated Nov. 20, 2015, in counterpart European Application No. 13738758.5, 8 pages.
(Continued)

*Primary Examiner* — Henry Crenshaw
(74) *Attorney, Agent, or Firm* — Seed Intellectual Property Law Group LLP (57) ABSTRACT

A freezing detection device to be applied to a liquid cooling apparatus including a liquid tank for storing a liquid whose freezing is to be detected and a cooling unit located inside the liquid tank to cool the liquid, the freezing detection device comprises: a temperature detecting unit located at a predetermined distance from the cooling unit; and a determining unit configured to determine whether or not the liquid has frozen around the temperature detecting unit based on an output from the temperature detecting unit, the determining unit determining whether or not the liquid has frozen around the temperature detecting unit based on whether the output from the temperature detecting unit is fluctuating or not.

17 Claims, 5 Drawing Sheets

(51) Int. Cl.
*F25D 21/06* (2006.01)
*F25B 5/00* (2006.01)
*A23L 3/36* (2006.01)
*F25D 21/02* (2006.01)
*F25D 31/00* (2006.01)
*G01K 7/16* (2006.01)
*B67D 1/08* (2006.01)
*G01N 25/06* (2006.01)
*G01N 33/14* (2006.01)

(52) U.S. Cl.
CPC ........... *G01N 25/06* (2013.01); *B67D 1/0859* (2013.01); *B67D 1/0878* (2013.01); *B67D 2210/00104* (2013.01); *F25B 2700/11* (2013.01); *F25D 2700/12* (2013.01); *G01N 33/146* (2013.01)

(58) Field of Classification Search
USPC ............................. 62/59, 138, 156, 199, 303
See application file for complete search history.

(56) References Cited

U.S. PATENT DOCUMENTS

| | | | | |
|---|---|---|---|---|
| 4,662,184 A * | 5/1987 | Pohl | ...................... | F25D 21/006 62/156 |
| 4,907,417 A * | 3/1990 | Forsythe | ............. | B67D 1/0864 62/199 |
| 4,932,222 A * | 6/1990 | Adams, Jr. | ................. | A01J 9/04 165/104.31 |
| 5,022,233 A * | 6/1991 | Kirschner | ............ | B67D 1/0864 62/138 |
| 5,839,291 A * | 11/1998 | Chang | .................. | B67D 1/0054 62/126 |
| 5,987,897 A * | 11/1999 | Hall | ...................... | B67D 1/0864 62/139 |
| 2002/0104322 A1* | 8/2002 | Horey | .................. | C12Q 1/6837 62/138 |
| 2005/0097913 A1* | 5/2005 | Hess | ...................... | A23G 9/045 62/340 |

FOREIGN PATENT DOCUMENTS

| | | |
|---|---|---|
| JP | 56-58650 A | 5/1981 |
| JP | 57-57809 A | 4/1982 |
| JP | 09-089546 A | 4/1997 |
| JP | 10-253210 A | 9/1998 |
| JP | 11-51531 A | 2/1999 |
| JP | 2004-116814 A | 4/2004 |
| JP | 2011-73775 A | 4/2011 |
| JP | 2011-122793 A | 6/2011 |

OTHER PUBLICATIONS

Communication pursuant to Article 94(3) EPC, dated Jul. 10, 2017, corresponding to European Application No. 13 738 758.5-1605, 5 pages.

* cited by examiner

FREEZING DETECTION DEVICE

BACKGROUND

Technical Field

The present invention relates to a freezing detection device to be applied to e.g. a beverage cooling apparatus for making beverages (e.g. beer) cold.

Description of the Related Art

Conventionally, at a restaurant or the like, when a beer server is used for pouring beer into mugs or glasses to serve customers, an ice thermal-storage cooling apparatus has been typically used for cooling the beer. For example, the ice thermal-storage cooling apparatus cools water (beverage cooling liquid) stored in a water tank provided inside the cooling apparatus by an evaporator of a vapor-compression refrigerator located in the water tank so that ice is formed around the evaporator for thermal storage, and cools beer by allowing the beer guided from a beer keg to pass through a pipe placed inside the water tank so that the beer is cooled to an appropriate temperature for drinking (e.g. about 5° C.). The use of ice thermal storage enables required beverage-cooling capability to be ensured while enabling a capacity of the vapor-compression refrigerator to be smaller.

In order to exert control in such a manner that the amount of ice formed around the evaporator reaches a predetermined amount, such an ice thermal-storage cooling apparatus is provided with a freezing detection device for detecting that the amount of ice formed around the evaporator has reached the predetermined amount. A conventional freezing detection device is provided with a pair of electrodes at a position corresponding to a desired amount of ice, and determines whether or not the water has frozen around the electrodes on the basis of a difference in electrical conductivity between water in a liquid state and water having frozen into a solid state, thereby determining whether or not the desired amount of ice has been formed.

Such a conventional freezing detection device, however, sometimes makes an incorrect determination that the desired amount of ice has been formed in spite of the fact that the desired amount of ice has not been formed, due to decrease in electrical conductivity of the water stored in the water tank, when the water stored in the water tank has changed in quality with the passage of time, and the amount of electrolyte contained in the water has decreased.

Furthermore, there are some sorts of beverage having an appropriate temperature for drinking (e.g. −2° C.) that is lower than the temperature to which a conventional ice thermal-storage cooling apparatus can cool the beverage. As an apparatus for cooling such beverages to the appropriate temperature for drinking, there is known an apparatus which utilizes an antifreeze liquid whose freezing temperature is lower than that of water, instead of water, as a beverage cooling liquid and cools the antifreeze liquid by a vapor-compression refrigerator to achieve the temperature of beverage which is lower than that achieved by a conventional ice thermal-storage cooling apparatus.

When using an antifreeze liquid as a beverage cooling liquid in such a manner, it is difficult to determine on the basis of a difference in electrical conductivity whether or not the antifreeze liquid has frozen because the antifreeze liquid, which is usually higher in electrical conductivity than water, exhibits a high electrical conductivity even in a frozen state.

Japanese Patent Application Laid-Open No. 2011-73775 describes a beer server including a freezing sensor located in the vicinity of an evaporator pipe in a water tank and configured to detect on the basis of change in electrical resistance (electrical conductivity) of water whether or not a predetermined thickness of ice has been formed around the evaporator pipe; and a beer server including a temperature sensor for freezing detection configured to detect whether or not a predetermined thickness of ice has been formed around an evaporator pipe through the use of a difference in temperature between cooling water and ice.

Patent Document 1: Japanese Patent Application Laid-Open No. 2011-73775 (¶¶ 0047, 0048, FIG. 2, ¶ 0080, FIG. 12)

An object of the present invention is to provide a freezing detection device capable of determining whether a liquid whose freezing is to be detected has frozen or not, irrespective of electrical conductivity of the liquid whose freezing is to be detected.

BRIEF SUMMARY

A freezing detection device according to the present invention is a freezing detection device to be applied to a liquid cooling apparatus including a liquid tank for storing a liquid whose freezing is to be detected and a cooling unit located inside the liquid tank to cool the liquid, and the freezing detection device comprises: a temperature detecting unit located at a predetermined distance from the cooling unit; and a determining unit configured to determine whether or not the liquid has frozen around the temperature detecting unit based on an output from the temperature detecting unit, the determining unit determining whether or not the liquid has frozen around the temperature detecting unit based on whether the output from the temperature detecting unit is fluctuating or not.

In the above case, the determining unit may be configured to determine that the liquid has not frozen around the temperature detecting unit when the output from the temperature detecting unit is fluctuating, and determine that the liquid has frozen around the temperature detecting unit when the output from the temperature detecting unit is not fluctuating. Furthermore, the determining unit may be configured to determine whether or not the liquid has frozen around the temperature detecting unit based on whether a temperature detected by the temperature detecting unit is fluctuating or not.

Furthermore, in the above cases, the temperature detecting unit may comprise a thermistor (e.g. NTC thermistor).

A liquid cooling apparatus according to the present invention comprises: a liquid tank for storing a liquid whose freezing is to be detected; a cooling unit located inside the liquid tank to cool the liquid; and the above-described freezing detection device.

In the above case, the liquid cooling apparatus may further comprise an agitator configured to stir the liquid stored in the liquid tank. Further, the cooling unit may comprise an evaporator of a vapor-compression refrigerator. Still further, the vapor-compression refrigerator may be controlled to operate when the determining unit determines that the liquid has not frozen around the temperature detecting unit, and to stop operating when the determining unit determines that the liquid has frozen around the temperature detecting unit.

Furthermore, the liquid may be e.g. water or an antifreeze liquid.

A beverage cooling apparatus according to the present invention comprises: the above-described liquid cooling apparatus; and a beverage-channel-defining section defining a beverage channel through which a beverage to be cooled is allowed to flow, the beverage-channel-defining section being located inside the liquid tank.

In the above case, the freezing detection device may determine whether or not a desired amount of ice has been formed around the cooling unit. Furthermore, the temperature detecting unit may be located at a position corresponding to the desired amount.

According to the present invention, it is possible to determine whether a liquid whose freezing is to be detected has frozen or not, irrespective of electrical conductivity of the liquid whose freezing is to be detected.

DETAILED DESCRIPTION

Hereinafter, an embodiment of the present invention will be described with reference to the drawings. The followings describe a case where the present invention is applied to a beverage cooling apparatus for cooling beer as a beverage (hereinafter, referred to as "beer cooling apparatus"). This beer cooling apparatus is used for cooling beer supplied from an outside source. More specifically, this beer cooling apparatus is configured to cool beer at a predetermined temperature (e.g. 25° C.) supplied from an outside source (e.g. a beer keg) to a predetermined appropriate temperature for drinking (e.g. about 5° C.), and supply the cooled beer to an outside destination (e.g. a pouring tap).

Figure 1:
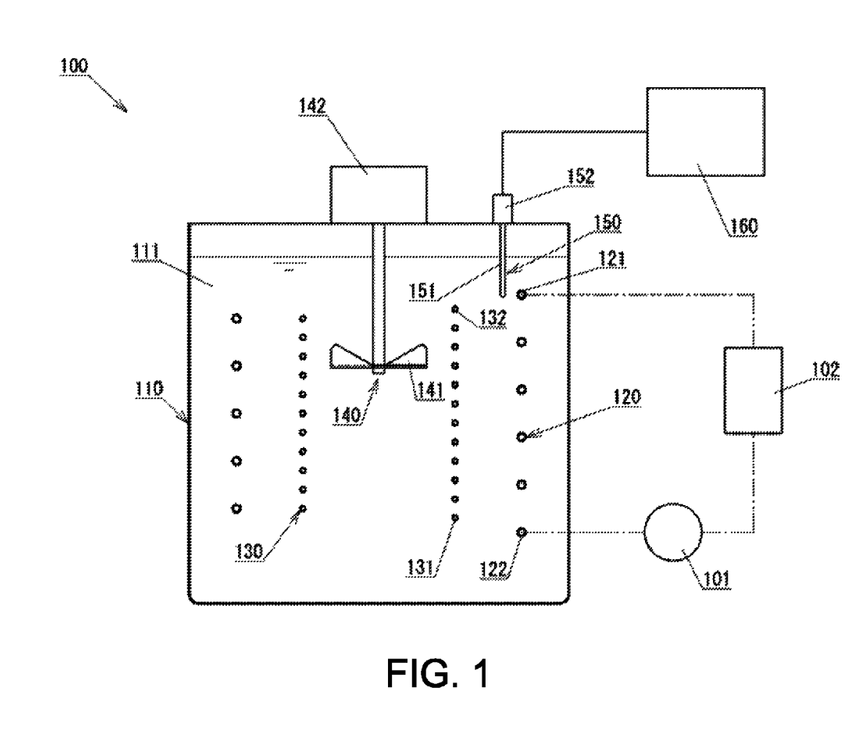
FIG. 1 is an explanatory view of a structure of a beer cooling apparatus incorporating a freezing detection device according to the present invention.

FIG. 1 is an explanatory view of a structure of a beer cooling apparatus incorporating a freezing detection device according to the present invention.

As shown in FIG. 1, the beer cooling apparatus 100, to which a freezing detection device according to the present invention is applied, includes a liquid tank 110, an ice-making pipe 120, a beverage cooling pipe 130, a cooling liquid agitator 140, a temperature detecting unit 150 and a control unit 160.

The liquid tank 110 is a container for storing a cooling liquid (water in the case of the present embodiment) 111 for cooling beer as a beverage to be cooled. In this embodiment, cooling liquid 111 is the subject of freezing detection by the freezing detection device according to the present invention.

The ice-making pipe 120 (cooling unit), located inside the liquid tank 110 to cool the cooling liquid 111 stored in the liquid tank 110, is in a shape of a pipe formed in a coiled (spiral) manner and allows a refrigerant (e.g. chlorofluorocarbon) to pass therethrough. It is to be noted that, for the sake of simplicity, FIG. 1 and the like show only a cross-section of the ice-making pipe 120. The ice-making pipe 120 comprises an evaporator of a vapor-compression refrigerator. The ice-making pipe 120 is connected to a compressor 101, a condenser 102, and the like to constitute a refrigeration cycle. A refrigerant introduced by operation of the compressor 101 into the ice-making pipe 120 through one end thereof (an end 121 located on the upper side in the case of this embodiment) evaporates inside the ice-making pipe 120 during passage therethrough, and heat absorption accompanying the evaporation cools the cooling liquid 111 stored in the liquid tank 110. Then, by continuing the operation of the compressor 101, the cooling liquid around the ice-making pipe 120 is caused to freeze, and ice (the cooling liquid having frozen into a solid state) will be formed around the ice-making pipe 120. The refrigerant discharged though the other end of the ice-making pipe 120 (an end 122 located on the lower side in the case of this embodiment) is returned to the compressor 101.

The beverage cooling pipe 130 (beverage-channel-defining section), located inside the liquid tank 110, defines a beverage channel through which a beverage (beer in the case of this embodiment) is allowed to pass, inside the liquid tank 110. By cooling the beverage cooling pipe 130 with the cooling liquid 111 stored in the liquid tank 110, beer supplied from an outside source into the beverage channel defined by the beverage cooling pipe 130 is cooled. The beverage cooling pipe 130 is in a shape of a pipe formed in a coiled (spiral) manner and allows beer to pass therethrough. It is to be noted that, for the sake of simplicity, FIG. 1 and the like show only a cross-section of the beverage cooling pipe 130, as in the case of the ice-making pipe 120. In this embodiment, the beverage cooling pipe 130 is formed such that a coil thereof is smaller in diameter than a coil of the ice-making pipe 120, and the coil formed by the beverage cooling pipe 130 is placed inside the coil formed by the ice-making pipe 120. Beer introduced from an outside source (e.g. a beer keg) into the beverage cooling pipe 130 through one end thereof (an end 131 located on the lower side in the case of this embodiment) is cooled to a predetermined temperature (e.g. 5° C.) by the cooling liquid 111 stored in the liquid tank 110 during passage through the beverage cooling pipe 130, and the beer thus cooled is delivered to an outside destination (e.g. a pouring tap) through the other end of the beverage cooling pipe 130 (an end 132 located on the upper side in the case of this embodiment).

The cooling liquid agitator 140 (agitator), configured to stir the cooling liquid 111 stored in the liquid tank 110 so that the cooling liquid 111 is uniformly cooled, includes a stirring fin 141 and a stirring motor 142. The stirring fin 141 is located inside the liquid tank 110 to stir the cooling liquid 111 stored in the liquid tank 110. The stirring motor 142 is connected to the stirring fin 140 to drive the stirring fin 141 to rotate. In this embodiment, the stirring fin 141 is located inside a hollow cylinder defined by the beverage cooling pipe 130, and rotation of the stirring fin 141 causes the cooling liquid to flow downward in the hollow cylinder defined by the beverage cooling pipe 130. When the cooling liquid flowing downward collides with a bottom surface of the liquid tank 110, then the cooling liquid is caused by the collision to flow outward. When the cooling liquid flowing outward collides with an inner circumferential surface of the liquid tank 110, then the cooling liquid is caused by the collision to flow upward. In other words, rotation of the stirring fin 141 causes the cooling liquid to flow downward inside the hollow cylinder defined by the beverage cooling pipe 130 and flow upward outside the hollow cylinder defined by the beverage cooling pipe 130. Generating such a flow of the cooling liquid facilitates uniformity of temperature of the cooling liquid 111 in the liquid tank 110.

The temperature detecting unit 150, along with the control unit 160, comprises the freezing detection device according to the present invention, and is placed in the vicinity of the ice-making pipe 120. The temperature detecting unit 150 includes a detecting unit 151 and a mounting section 152. The detecting unit 151 has its tip (temperature detecting portion) located in the vicinity of the ice-making pipe 120 to detect the temperature of an area around the tip. In this embodiment, the detecting unit 151 is obtained by placing a thermistor (NTC thermistor in the case of this embodiment) in an inside (tip portion) of a cylindrical stainless-steel case. The mounting section 152 fixes the detecting unit 151 such that the tip of the detecting unit 151 is located at a predetermined position. The temperature detecting unit 150 is mounted on the liquid tank 110 such that the tip of the detecting unit 151 is located at a position corresponding to a desired amount of ice.

The control unit 160 controls the operation of the beer cooling apparatus 100. In this embodiment, the functions of the control unit 160 are basically implemented by a microprocessor. Furthermore, as described above, the control unit 160, along with the temperature detecting unit 150, comprises the freezing detection device according to the present invention. In other words, the control unit 160 comprises a determining unit configured to determine whether or not a liquid whose freezing is to be detected (the cooling liquid 111 in the case of this embodiment) has frozen around the temperature detecting unit 150 based on an output from the temperature detecting unit 150.

Figure 2:
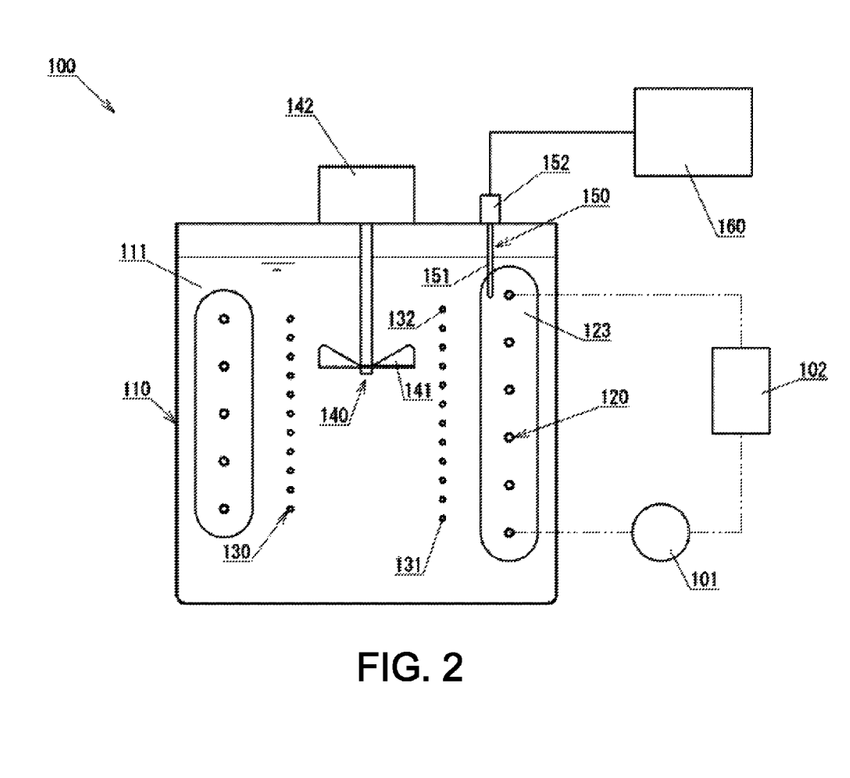
FIG. 2 is a view showing a state where ice has been formed around an ice-making pipe 120.

FIG. 2 is a view showing a state where ice has been formed around the ice-making pipe 120. FIG. 2 shows a state where the desired amount of ice has been formed.

As shown in FIG. 2, in a state where the desired amount of ice 123 has been formed around the ice-making pipe 120, ice is also formed around the tip (a portion at which the NTC thermistor is located) of the temperature detecting unit 150, with the result that the tip of the temperature detecting unit 150 comes to be buried in the ice 123. In other words, the temperature detecting unit 150 is located at such a position that its tip (temperature detecting portion) is buried in the ice 123 at a point in time when the desired amount of ice 123 has been formed around the ice-making pipe 120.

The followings describe how the beer cooling apparatus 100 having the above structures operates.

When the power of the beer cooling apparatus 100 is turned on, the control unit 160 starts the operation of the compressor 101. When the compressor 101 starts operating, a refrigerant introduced into the ice-making pipe 120 through the condenser 102 and an expansion valve (not shown) evaporates to cool the cooling liquid 111 stored in the liquid tank 110. Then, by continuing the operation of the compressor 101 so as to continuously cool the cooling liquid 111 stored in the liquid tank 110, ice is caused to start being formed around the ice-making pipe 120 after a while. Then, by further continuing the operation of the compressor 101 so as to continuously cool the cooling liquid 111 stored in the liquid tank 110, the ice formed around the ice-making pipe 120 is caused to grow and eventually reach the tip of the temperature detecting unit 150, with the result that, as shown in FIG. 2, the tip of the temperature detecting unit 150 comes to be buried in the ice 123.

For example, upon appropriate detection of decreasing of the temperature of the cooling liquid 111 to a predetermined temperature (e.g. a freezing temperature), the control unit 160, which comprises the freezing detection device along with the temperature detecting unit 150, starts monitoring whether or not the tip of the temperature detecting unit 150 has been buried in ice based on an output signal from the temperature detecting unit 150. Then, upon detection of the fact that the tip of the temperature detecting unit 150 has been buried in ice, i.e., the state where a predetermined amount of ice has been formed, the control unit 160 stops the operation of the compressor 101. Then, on the basis of an output signal from the temperature detecting unit 150, the control unit 160 appropriately monitors whether the ice formed around the ice-making pipe 120 has melted to the extent that the tip of the temperature detecting unit 150 is exposed out of the ice. Then, upon detection of the fact that the tip of the temperature detecting unit 150 is exposed out of the ice, i.e., the state where the amount of ice formed around the ice-making pipe 120 is less than the predetermined amount, the control unit 160 starts the operation of the compressor 101 again. In such a manner, after the predetermined amount of ice has been formed around the ice-making pipe 120, the control unit 160 performs the on-off control of the compressor 101 such that the predetermined amount of ice is maintained.

In a state where the predetermined amount of ice 123 has been formed around the ice-making pipe 120, beer introduced into the beverage cooling pipe 130 through the one end 131 thereof is cooled to a desired temperature (e.g. 5° C.) by the cooling liquid 111 stored in the liquid tank 110 during passage through the beverage cooling pipe 130 to be delivered from the other end 132 thereof.

The followings describe how the freezing detection device according to the present invention operates.

Figure 3:
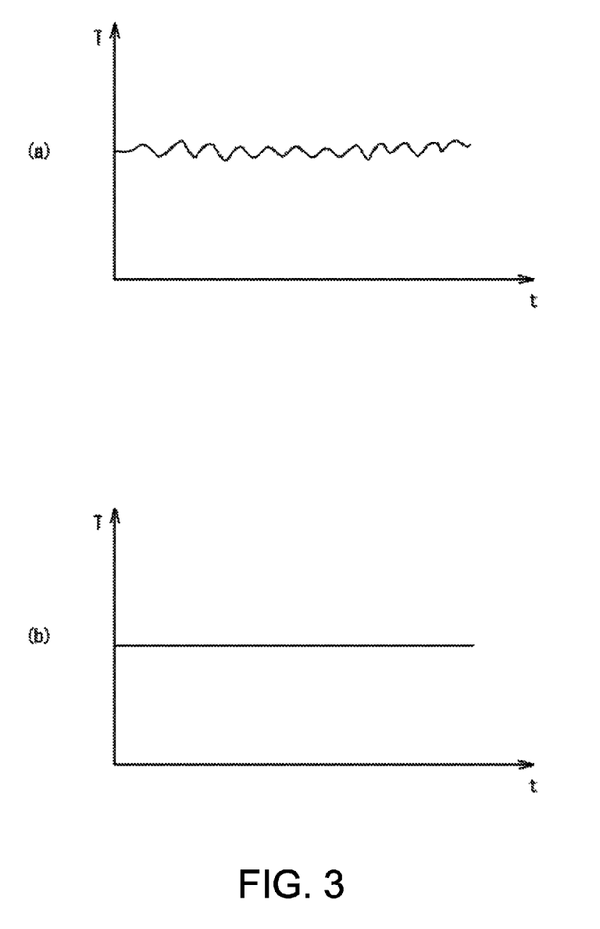
FIG. 3 is time-dependent temperature graphs each showing how the temperature detected by a temperature detecting unit 150 varies as a function of time.

FIG. 3 is time-dependent temperature graphs each showing how the temperature detected by a temperature detecting unit 150 varies as a function of time. In each graph of FIG. 3, the horizontal axis represents time (t), and the vertical axis represents temperature (T). The graph (a) in FIG. 3 shows time variation of temperature when ice has been formed around the ice-making pipe 120 but has not reached an area around the tip of the temperature detecting unit 150. The graph (b) in FIG. 3 shows time variation of temperature when the ice formed around the ice-making pipe 120 has grown to reach an area around the tip of the temperature detecting unit 150 as shown in FIG. 2.

When the ice formed around the ice-making pipe 120 has not reached an area around the tip of the temperature detecting unit 150, the tip (a portion at which the NTC thermistor is located) of the temperature detecting unit 150 is exposed to the cooling liquid 111. As described above, since the cooling liquid 111 stored in the liquid tank 110 is stirred by the cooling liquid agitator 140, there is a flow of the cooling liquid 111 inside the liquid tank 110. In other words, the tip of the temperature detecting unit 150 is always subjected to collision with the flow of the cooling liquid 111. Meanwhile, since the cooling liquid 111 stored in the liquid tank 110 is cooled gradually from an area around the ice-making pipe 120, there occurs a certain degree of temperature difference depending upon regions inside the liquid tank 110. Therefore, the stirring of the cooling liquid 111 by the cooling liquid agitator 140 gives rise to a certain degree of temperature difference for the cooling liquid colliding with the tip of the temperature detecting unit 150. As a result, as shown in the graph (a) in FIG. 3, the temperature detected by the temperature detecting unit 150 fluctuates within a certain range with the passage of time.

Meanwhile, when the cooling of the cooling liquid 111 by the ice-making pipe 120 proceeds, and the ice formed on the surface of the ice-making pipe 120 grows to reach the tip of the temperature detecting unit 150, with the result that the tip of the temperature detecting unit 150 is buried in the ice, a flow of the cooling liquid no longer collides with the tip of the temperature detecting unit 150. As a result, as shown in the graph (b) in FIG. 3, the temperature detected by the temperature detecting unit 150 no longer varies as a function of time.

The freezing detection device according to the present invention discriminates such a difference in temporal variation of the temperature detected by the temperature detecting unit 150, thereby determining whether or not the tip of the temperature detecting unit 150 has been buried in ice, i.e., whether or not the cooling liquid has frozen around the tip of the temperature detecting unit 150. In other words, when the temperature detected by the temperature detecting unit 150 is fluctuating, the freezing detection device determines that the tip of the temperature detecting unit 150 is not buried in ice, i.e., no ice is formed in the proximity of the tip of the temperature detecting unit 150. On the other hand, when the temperature detected by the temperature detecting unit 150 is not fluctuating, the freezing detection device determines that the tip of the temperature detecting unit 150 is buried in ice, i.e., ice has been formed around the tip of the temperature detecting unit 150.

Figure 4:
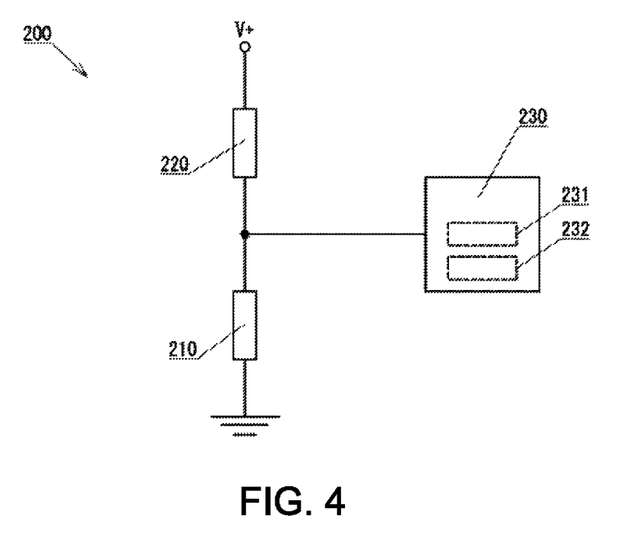
FIG. 4 is a diagram showing an example configuration of a temperature detecting circuit used for realizing the freezing detection device according to the present invention.

FIG. 4 is a diagram showing an example configuration of a temperature detecting circuit used for realizing the freezing detection device according to the present invention.

As shown in FIG. 4, the temperature detecting circuit 200 includes an NTC thermistor 210, a resistor 220, and a microprocessor 230. The NTC thermistor 210 comprises the temperature detecting unit 150, and the microprocessor 230 comprises the control unit 160. Further, the NTC thermistor 210 has one terminal grounded, and has the other terminal connected to one terminal of the resistor 220 as well as an analog input terminal of the microprocessor 230. Still further, the resistor 220 has the other terminal connected to a power supply voltage V+.

In such a temperature detecting circuit 200 as shown in FIG. 4, a variation of resistance value of the NTC thermistor 210 occurring in accordance with a variation of ambient temperature leads to a variation of voltage value of a signal input to the microprocessor 230.

The microprocessor 230 has an ND converter 231 incorporated therein, and the voltage value (analog data) of a signal input through the analog input terminal is converted appropriately by the ND converter 231 into digital data. The microprocessor 230 operates the ND converter 231 at regular intervals (e.g. every 0.1 second) so as to convert the voltage value of a signal input through the analog input terminal into digital data, and further converts the digitized voltage value into a temperature (temperature data) in accordance with a conversion table prepared in advance (sampling). A plurality of pieces of temperature data thus obtained are stored in sequence by the microprocessor 230 in a temperature data storage area allocated in an internal memory 232 of the microprocessor 230 (or in an external memory which is not shown). For the temperature data storage area, such a size is reserved that a predetermined amount of temperature data (e.g. 100 pieces of temperature data) over a predetermined period of time (e.g. 10 seconds) can be stored. Furthermore, the temperature data storage area is managed in such a manner that the temperature data storage area forms a ring buffer, and that, after a predetermined period of time (e.g. 10 seconds) has elapsed, a predetermined amount (e.g. 100 pieces) of the most recent temperature data over a predetermined period of time (e.g. 10 seconds) is always stored in the temperature data storage area.

Figure 5:
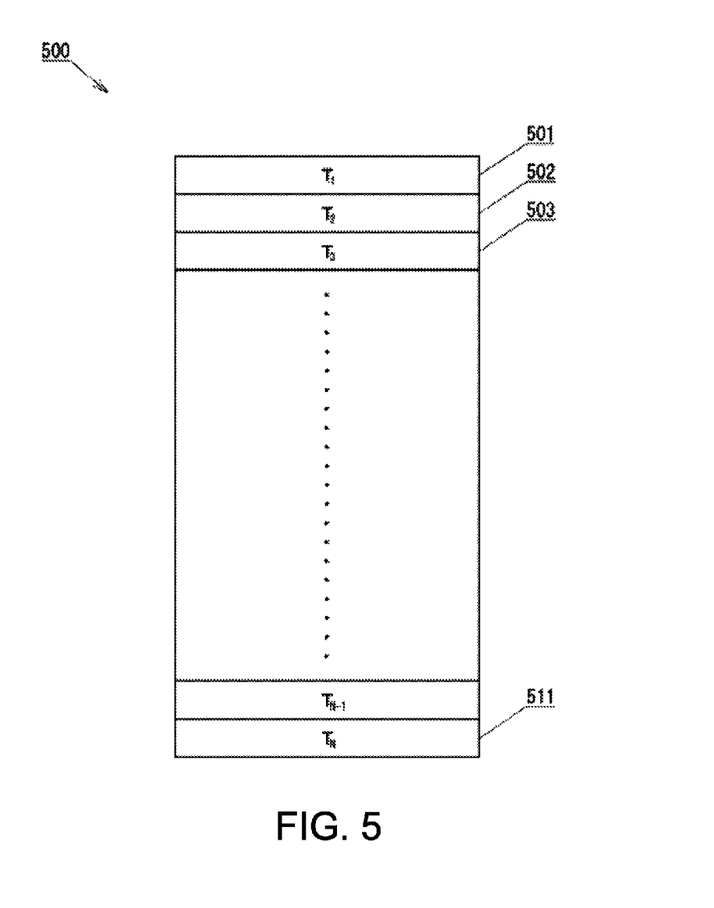
FIG. 5 is an explanatory diagram of a structure of a temperature data storage area.

FIG. 5 is an explanatory diagram of a structure of a temperature data storage area.

As shown in FIG. 5, the temperature data storage area 500 is a data storage area having such a size that a predetermined amount of temperature data $T_1$ to $T_N$ (N pieces of temperature data in the example shown in FIG. 5) can be stored.

For example, initially, upon obtaining temperature data $T_1$ at a time $t_1$ through sampling at the time $t_1$ as a sampling start time, the microprocessor 230 stores the temperature data $T_1$ in an area 501 located at the top of the temperature data storage area 500. Subsequently, upon obtaining temperature data $T_2$ at a time $t_2$ through sampling at the time $t_2$ as a sampling time subsequent to the time $t_1$, the microprocessor 230 stores the temperature data $T_2$ in an area 502 located subsequently to the area 501. Subsequently, upon obtaining temperature data $T_3$ at a time $t_3$ through sampling at the time $t_3$ as a sampling time subsequent to the time $t_2$, the microprocessor 230 stores the temperature data $T_3$ in an area 503 located subsequently to the area 502. The microprocessor 230 repeats such a process at each sampling time. Then, upon obtaining the Nth piece of temperature data $T_N$ through sampling at a time $t_N$ when a predetermined period of time has elapsed since the sampling start time, the microprocessor 230 stores the temperature data $T_N$ in an area 511 located at the bottom of the temperature data storage area 500. As a result, as shown in FIG. 5, N pieces of temperature data $T_1$ to $T_N$ over the predetermined period of time, i.e., the time $t_1$ to time $t_N$ are stored in the temperature data storage area 500.

Further, in the state shown in FIG. 5, upon obtaining temperature data $T_{N+1}$ at a time $t_{N+1}$ through sampling at the time $t_{N+1}$ as a sampling time subsequent to the time $t_N$, the microprocessor 230 returns to the area 501 located at the top to store the temperature data $T_{N+1}$ in the area 501. As a result, N pieces of the most recent temperature data $T_2$ to $T_{N+1}$ over the time $t_2$ to time $t_{N+1}$ are stored in the temperature data storage area 500. In this case, logically (chronologically), the area 502 is the first area and the area 501 is the last area while the areas 503, 511, and the like are therebetween. Still further, upon obtaining temperature data $T_{N+2}$ at a time $t_{N+2}$ through sampling at the time $t_{N+2}$ as a sampling time subsequent to the time $t_{N+1}$, the microprocessor 230 stores the temperature data $T_{N+2}$ in the area 502 located subsequently to the area 501. As a result, N pieces of the most recent temperature data $T_3$ to $T_{N+2}$ over the time $t_3$ to time $t_{N+2}$ are stored in the temperature data storage area 500. In this case, logically (chronologically), the area 503 is the first area and the area 502 is the last area while the areas 511, 501, and the like are therebetween. Through repetition of such a process at each sampling time, N pieces of the most recent temperature data over a predetermined period of time are always stored in the temperature data storage area 500. The addresses of the logically (chronologically) first and last areas are managed appropriately by the microprocessor 230.

Upon completion of collection of a predetermined amount of temperature data (e.g. 100 pieces of temperature data) over a predetermined period of time (e.g. 10 seconds), the microprocessor 230 appropriately performs a filtering process on the temperature data stored in the temperature data storage area 500 to remove noise, and thereafter determines whether or not the temperature data stored in the temperature data storage area 500 is varying with the passage of time. For example, the microprocessor 230 sequentially adds up the absolute values of differences between temporally-adjacent pieces of temperature data, respectively, so as to calculate the sum of the absolute values. In other words, the microprocessor 230 calculates the sum S represented by Expression 1 as follows:

$$S = \sum_{i=1}^{N-1} |T_i - T_{i+1}| \quad (1)$$

The above symbol, Ti (i=1 to N), denotes each piece of temperature data stored in the temperature data storage area 500, where $T_1$ denotes the oldest piece of temperature data stored in the temperature data storage area 500, and $T_N$ denotes the most recent piece of temperature data stored in the temperature data storage area 500.

Then, the microprocessor 230 determines whether or not the sum S thus calculated is greater than or equal to a predetermined threshold value. If the sum S is greater than or equal to the predetermined threshold value, the microprocessor 230 determines that the temperature is varying with the passage of time (i.e. the NTC thermistor 210 is not buried in ice). On the other hand, if the sum S is less than the predetermined threshold value, the microprocessor 230 determines that the temperature is not varying (over a predetermined period of time) (i.e. the NTC thermistor 210 is buried in ice). The determination as to whether or not the temperature data stored in the temperature data storage area 500 is varying with the passage of time is made at an appropriate timing in accordance with implementation conditions such as the cycle of fluctuation in temperature, the sampling cycle, and the processing speed of the microprocessor 230. In this embodiment, the determination is made every time a sampling time comes, and the latest temperature data is stored in the temperature data storage area 500, i.e., every time one of a predetermined number of pieces of temperature data (e.g. 100 pieces of temperature data) over a predetermined period of time (e.g. 10 seconds) stored in the temperature data storage area 500 is updated.

In such a manner, it is determined whether or not the tip (NTC thermistor 210) of the temperature detecting unit 150 has been buried in ice, i.e., whether or not a desired amount of ice has been formed.

As described above, in the above-described freezing detection device, it is determined whether or not the tip of the temperature detecting unit 150 has been buried in ice, i.e., whether or not a desired amount of ice has been formed, on the basis of whether or not the temperature detected by the temperature detecting unit 150 is fluctuating (within a predetermined period of time), which enables the freezing detection device to detect the formation of the desired amount of ice irrespective of the electrical conductivity of the cooling liquid 111. For example, therefore, even if the electrical conductivity of the cooling liquid stored in the liquid tank changes with the passage of time, it is possible to determine correctly whether or not the desired amount of ice has been formed. Further, even when an antifreeze liquid exhibiting a high electrical conductivity even in a frozen state is used as the cooling liquid, it is possible to determine whether or not the desired amount of ice has been formed.

Embodiments of the present invention have been described thus far; however, the present invention is of course not limited to the above-described embodiments. For example, although the temperature detecting unit is constituted by an NTC thermistor in the embodiment described above, the temperature detecting unit may alternatively be constituted by other temperature detection means (e.g. a platinum resistance temperature sensor or a thermocouple).

Further, although a digitized voltage value is further converted into temperature data in the embodiment described above, the digitized voltage value may be directly used to determine whether or not the tip of the temperature detecting unit 150 has been buried in ice on the basis of whether the voltage value is fluctuating or not.

Still further, although the temperature detecting unit 150 has its tip (temperature detecting portion) located in the vicinity of the end 121 which is on the upper side of the ice-making pipe 120 in the embodiment described above, the temperature detecting unit 150 may alternatively have its tip located at any other position corresponding to a desired amount of ice e.g. in the vicinity of the end 122 which is on the lower side of the ice-making pipe 120.

Still further, although water is used as the cooling liquid to be stored in the liquid tank 110 in the embodiment described above, other liquid (e.g. an antifreeze liquid) may alternatively be used.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A freezing detection device to be applied to a liquid cooling apparatus including a liquid tank for storing a liquid whose freezing is to be detected, a cooling unit located inside the liquid tank to cool the liquid and an agitator configured to stir the liquid stored in the liquid tank, the freezing detection device comprising:
   a temperature detecting unit located at a predetermined distance from the cooling unit; and
   a determining unit configured to determine whether or not the liquid has frozen around the temperature detecting unit based on an output from the temperature detecting unit,
   the determining unit being adapted to determine whether or not the liquid has frozen around the temperature detecting unit based on whether the output from the temperature detecting unit is fluctuating or not as a result of temperature differences in the liquid colliding with the temperature detecting unit.

2. The freezing detection device according to claim 1, wherein the determining unit
   determines that the liquid has not frozen around the temperature detecting unit when the output from the temperature detecting unit is fluctuating, and
   determines that the liquid has frozen around the temperature detecting unit when the output from the temperature detecting unit is not fluctuating.

3. The freezing detection device according to claim 1, wherein the determining unit is adapted to determine whether or not the liquid has frozen around the temperature detecting unit based on whether a temperature measured by the temperature detecting unit is fluctuating or not.

4. The freezing detection device according to claim 2, wherein the determining unit is adapted to determine whether or not the liquid has frozen around the temperature detecting unit based on whether a temperature measured by the temperature detecting unit is fluctuating or not.

5. The freezing detection device according to claim 1, wherein the temperature detecting unit comprises a thermistor.

6. The freezing detection device according to claim 2, wherein the temperature detecting unit comprises a thermistor.

7. The freezing detection device according to claim 3, wherein the temperature detecting unit comprises a thermistor.

8. The freezing detection device according to claim 4, wherein the temperature detecting unit comprises a thermistor.

9. A liquid cooling apparatus comprising:
a liquid tank for storing a liquid whose freezing is to be detected;
a cooling unit located inside the liquid tank to cool the liquid;
an agitator configured to stir the liquid stored in the liquid tank; and
a freezing detection device comprising
a temperature detecting unit located at a predetermined distance from the cooling unit, and
a determining unit configured to determine whether or not the liquid has frozen around the temperature detecting unit based on an output from the temperature detecting unit,
the determining unit determining whether or not the liquid has frozen around the temperature detecting unit based on whether the output from the temperature detecting unit is fluctuating or not as a result of temperature differences in the liquid colliding with the temperature detecting unit.

10. The liquid cooling apparatus according to claim 9, wherein the determining unit
determines that the liquid has not frozen around the temperature detecting unit when the output from the temperature detecting unit is fluctuating, and
determines that the liquid has frozen around the temperature detecting unit when the output from the temperature detecting unit is not fluctuating.

11. The liquid cooling apparatus according to claim 9, wherein the cooling unit comprises an evaporator of a vapor-compression refrigerator.

12. The liquid cooling apparatus according to claim 11, wherein the vapor-compression refrigerator is controlled to operate when the determining unit determines that the liquid has not frozen around the temperature detecting unit, and
stop operating when the determining unit determines that the liquid has frozen around the temperature detecting unit.

13. The liquid cooling apparatus according to claim 9, wherein the liquid is an antifreeze liquid.

14. A beverage cooling apparatus comprising:
a liquid cooling apparatus comprising
a liquid tank for storing a liquid whose freezing is to be detected,
a cooling unit located inside the liquid tank to cool the liquid,
an agitator configured to stir the liquid stored in the liquid tank, and
a freezing detection device comprising
a temperature detecting unit located at a predetermined distance from the cooling unit, and
a determining unit configured to determine whether or not the liquid has frozen around the temperature detecting unit based on an output from the temperature detecting unit,
the determining unit determining that the liquid has not frozen around the temperature detecting unit when the output from the temperature detecting unit is fluctuating as a result of temperature differences in the liquid colliding with the temperature detecting unit and determining that the liquid has frozen around the temperature detecting unit when the output from the temperature detecting unit is not fluctuating as a result of a temperature detecting portion of the temperature detecting unit being buried in the frozen liquid; and
a beverage-channel-defining section defining a beverage channel through which a beverage to be cooled is allowed to flow,
the beverage-channel-defining section being located inside the liquid tank.

15. The beverage cooling apparatus according to claim 14, wherein the freezing detection device determines whether or not a desired amount of ice has been formed around the cooling unit.

16. The beverage cooling apparatus according to claim 15, wherein the temperature detecting unit is located at a position corresponding to the desired amount.

17. The beverage cooling apparatus according to claim 14, wherein the liquid is an antifreeze liquid.

* * * * *